(12) United States Patent
Naderer et al.

(10) Patent No.: US 10,737,141 B2
(45) Date of Patent: Aug. 11, 2020

(54) DEVICE FOR TRAINING COORDINATIVE FACULTIES

(71) Applicant: Ferrobotics Compliant Robot Technology GmbH, Linz (AT)

(72) Inventors: Ronald Naderer, St. Florian (AT); Paolo Ferrara, Kematen an der Krems (AT)

(73) Assignee: Ferrobotics Compliant Robot Technology GmbH, Lina (AT)

( * ) Notice: Subject to any disclaimer, the term of this patent is extended or adjusted under 35 U.S.C. 154(b) by 151 days.

(21) Appl. No.: 15/947,982

(22) Filed: Apr. 9, 2018

(65) Prior Publication Data

US 2018/0290022 A1 Oct. 11, 2018

Related U.S. Application Data

(63) Continuation of application No. 14/430,285, filed as application No. PCT/AT2013/050188 on Sep. 18, 2013, now Pat. No. 9,956,452.

(30) Foreign Application Priority Data

Sep. 21, 2012 (DE) .................. 10 2012 108 957

(51) Int. Cl.
*A63B 24/00* (2006.01)
*A61B 5/103* (2006.01)
(Continued)

(52) U.S. Cl.
CPC ........ *A63B 24/0075* (2013.01); *A61B 5/0037* (2013.01); *A61B 5/1036* (2013.01);
(Continued)

(58) Field of Classification Search
CPC ............ A63B 22/16–18; A63B 26/003; A61B 5/1036; A61B 5/4023
See application file for complete search history.

(56) References Cited

U.S. PATENT DOCUMENTS

| | | | | |
|---|---|---|---|---|
| 5,830,158 A | * | 11/1998 | Zanakis | A61B 5/1036 600/595 |
| 7,004,895 B2 | * | 2/2006 | Perry | A61H 1/005 482/146 |

(Continued)

*Primary Examiner* — Jennifer Robertson
(74) *Attorney, Agent, or Firm* — Muirhead and Saturnelli, LLC

(57) ABSTRACT

The invention relates to a device for training coordinative faculties. The device has at least one movable standing plate; at least one static base plate; at least two connecting elements, the height of which can be modified and which act between the at least one movable standing plate and the at least one static base plate, a user interface; and a control element. The device is designed to specify a sequence of various setpoint positions of the centre of gravity of a user standing on the at least one movable standing plate, each of the setpoint positions being specified for a determined duration, and to continuously measure the actual position of the centre of gravity of the person standing on the moving plate. The device is further designed to compare each measured actual position to the setpoint position specified at the time of the measurement, to generate control signals taking into consideration the measured actual positions and/or the results of the comparisons of actual positions and setpoint positions, and to control the at least two connecting elements with the control signals.

19 Claims, 4 Drawing Sheets

(51) Int. Cl.
*A63B 22/00* (2006.01)
*A63B 22/16* (2006.01)
*A63B 69/00* (2006.01)
*A61B 5/00* (2006.01)
*A63B 22/18* (2006.01)
*A63B 26/00* (2006.01)
*A63B 71/06* (2006.01)

(52) U.S. Cl.
CPC ........ *A61B 5/4023* (2013.01); *A63B 22/0015* (2013.01); *A63B 22/0023* (2013.01); *A63B 22/16* (2013.01); *A63B 22/18* (2013.01); *A63B 24/0006* (2013.01); *A63B 24/0062* (2013.01); *A63B 24/0087* (2013.01); *A63B 26/003* (2013.01); *A63B 69/0053* (2013.01); *A63B 71/0619* (2013.01); *A63B 2024/0012* (2013.01); *A63B 2024/0015* (2013.01); *A63B 2024/0065* (2013.01); *A63B 2024/0068* (2013.01); *A63B 2024/0093* (2013.01); *A63B 2220/18* (2013.01); *A63B 2220/52* (2013.01); *A63B 2220/62* (2013.01)

(56) References Cited

U.S. PATENT DOCUMENTS

2008/0242521 A1* 10/2008 Einav .................... A61B 5/1116
 482/110
2011/0039669 A1* 2/2011 Stewart ................ A63B 21/015
 482/146

* cited by examiner

DEVICE FOR TRAINING COORDINATIVE FACULTIES

RELATED APPLICATIONS

This application is a continuation of U.S. application Ser. No. 14/430,285 filed Mar. 23, 2015, which is a National Stage of International App. No. PCT/AT2013/050188 filed Sep. 18, 2013, which claims priority to German application DE 10 2012 108957.4 filed Sep. 21, 2012, which are all incorporated herein by reference.

TECHNICAL FIELD

This application relates to a device for training coordinative faculties of individuals, in particular for training coordinative faculties of humans or animals using an unstable support base.

BACKGROUND OF THE INVENTION

Various devices are known which, by means of an unstable support base, train the coordinative faculties of persons. Such training may be necessary, for example, for sports purposes, educational purposes or therapeutic purposes. However, training for purely enjoyment purposes is also conceivable. Generally, in such devices, an individual (i.e. a person or an animal) standing on a movable plate is made to balance such that the plate remains horizontal.

DE 100 04 785 B4, for example, describes a training apparatus with a platform which is mounted movably about two horizontal axes lying in one plane and perpendicular to each other. A person standing on the apparatus has to actively compensate for an instability that is generated by the movable bearing. The extent of movement, the movement resistance and the inertia of the platform can be adjusted mechanically, by adapting suitable devices on the apparatus.

AT 411 015 B describes a training apparatus for improving and training the sense of balance. In this apparatus, a platform is provided which, mounted on its underside, has two arc-shaped rockers. By rolling on the rockers, the platform can be moved in a harmonious, controlled see-saw movement. After stepping off the training apparatus, it is possible to change the degree of difficulty by adjusting the position of the rockers, as a result of which the tilting behavior of the platform becomes gentler or more abrupt.

WO 2007/035976 A2 discloses a device for moving humans or other objects, which device has a static base surface and a moved surface. Active, controllable, mechanical actuating elements act between the static and moved surfaces. Various predefinable movement patterns can be actively performed in several degrees of freedom of the movement. The movement patterns can be controlled by a computer. The degree of difficulty can be adapted by suitable selection of a program.

Although a degree of difficulty can be adjusted in principle in the known training apparatuses, it has to be adjusted by the user himself and may therefore possibly be chosen incorrectly. For example, if too easy a degree of difficulty is chosen, the training may not be demanding enough and therefore boring, and, if the chosen degree of difficulty is too difficult, the training may be too demanding and therefore demotivating. Improved performance during training has to be detected actively by the user, and the degree of difficulty has to be accordingly adapted manually by the user. Particularly when such training devices are used on animals, it is not at all possible to gain any feedback concerning the degree of difficulty.

Accordingly, it would be desirable to provide a training apparatus which can detect the degree of difficulty appropriate to the individual and makes it possible to adapt the applied degree of difficulty.

SUMMARY OF THE INVENTION

A device for training coordinative faculties is described, with at least one movable standing plate, at least one static base plate, at least two connecting elements, the height of which can be modified and which act between the at least one movable standing plate and the at least one static base plate, a user interface, and a control element. The device is configured to specify a succession of various setpoint positions of the center of gravity of a user present on the at least one movable standing plate, wherein each of the setpoint positions is specified up to the onset of a certain event (e.g. time period elapsed, points score reached, stable position reached, setpoint position reached, etc.). The device is furthermore configured to measure continuously or calculate the actual position of the center of gravity of the user present on the movable standing plate, and to compare each measured actual position with the setpoint position specified at the time of its measurement. On the basis of the measured actual positions and/or the results of the comparisons of actual positions and setpoint positions, control signals can be generated, and the at least two connecting elements can be controlled with the control signals. Measurement is also understood quite generally as an indirect measurement in which the actual measurement result (the center of gravity) is calculated from other measured parameters.

Moreover, a method is described for operating a device for training coordinative faculties, with at least one movable standing plate, at least one static base plate, at least two connecting elements, the height of which can be modified and which act between the movable standing plate and the static base plate, a user interface, and a control element. The method comprises specifying a succession of various setpoint positions of the center of gravity of a user present on the at least one movable standing plate, wherein each of the setpoint positions is specified until specified events occur (e.g. time period elapsed, points score reached, etc.). The method furthermore comprises measuring continuously or calculating the actual position of the center of gravity of the user present on the at least one movable standing plate, and comparing each measured actual position with the setpoint position specified at the time of measurement. The method also comprises generating control signals, on the basis of the measured actual positions and/or the results of the comparisons of actual positions and setpoint positions, and controlling the at least two connecting elements with the control signals.

BRIEF DESCRIPTION OF THE DRAWINGS

The accompanying figures and the rest of the description are intended to provide a better understanding of the. More details, variants and developments of the concept of the are explained with reference to the. The details provided are not intended to limit the invention; instead, they are intended to help explain the underlying principle of the invention. Identical reference signs designate identical or similar components having the same or similar meaning. In the figures.

DETAILED DESCRIPTION OF VARIOUS EMBODIMENTS

Figure 1:
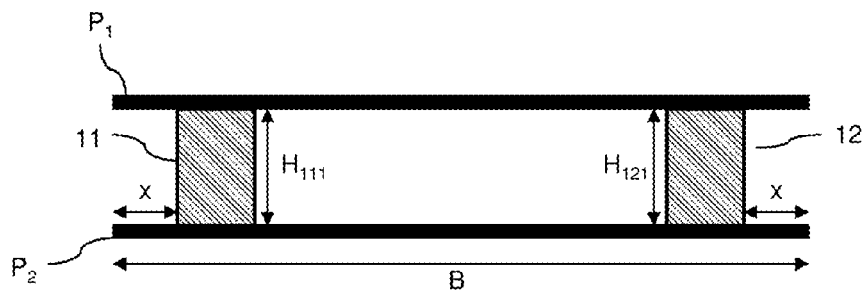
FIG. 1 shows by way of example the general principle of a device for training coordinative faculties with a movable standing plate.
Figure 2:
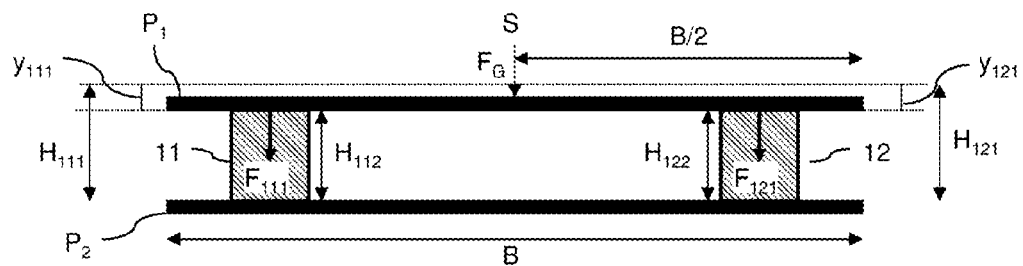
FIG. 2 shows by way of example the general principle of a device for training coordinative faculties with a movable standing plate.

FIGS. 1 to 4 show by way of example the basic principle of a device for training coordinative faculties with a movable standing plate. For this purpose, a device is shown in a simplified side view. A movable standing plate $P_1$ is connected to a fixed base plate $P_2$. In the view shown, this connection is implemented by two connecting elements 11, 12. However, it is also possible to provide more than two connecting elements 11, 12 in different arrangements. In an unloaded starting state of the movable standing plate $P_1$, the connecting elements 11, 12 have a height $H_{111}$ or $H_{121}$, respectively. FIG. 1 shows such an unloaded starting state of the device. The height $H_{111}$ of the connecting element 11 is identical to the height $H_{121}$ of the connecting element 12 ($H_{111}=H_{121}$).

In the unloaded starting state, the movable standing plate $P_1$, in the example shown in FIG. 1, therefore lies horizontally on the connecting elements 11, 12. A starting state of this kind is expedient for most uses, although it is also conceivable that the connecting elements 11, 12, in the unloaded starting state, have a different height $H_{111}$ and $H_{121}$, and the movable standing plate $P_1$ is not therefore oriented horizontally. In the example shown, the movable standing plate $P_1$ and the fixed base plate $P_2$ have an identical width B, although this does not necessarily have to be the case. The connecting elements 11, 12 are mounted at an identical distance x from the respective edge of the plates $P_1$ and $P_2$, although they can also be at different distances from the respective plate edges.

The connecting elements 11, 12 are configured in such a way that they are variable in terms of their height H under the action of a force F. When the height H of the connecting elements 11, 12 changes, the movable standing plate moves in the vertical direction. If both connecting elements 11, 12 are changed differently in terms of their height H, or if only one of the connecting elements 11 or 12 is changed in terms of its height, the movable standing plate $P_1$ slopes in the respective direction of the connecting element 11 or 12 that has the lower height H. In the arrangement shown, a slope of the movable standing plate $P_1$ is possible only about a horizontal axis. However, by the provision of further connecting elements which are arranged correspondingly between the plates $P_1$, $P_2$, a sloping of the movable standing plate $P_1$ can be permitted about several axes at a defined angle to each other.

If a user (i.e. a person, or possibly an animal) stands on the device, a force $F_G$ caused by the weight of the user acts on the movable standing plate $P_1$. This force $F_G$ thus also acts on the connecting elements 11, 12, such that the latter are reduced in height H. If the connecting elements 11, 12 are of identical configuration, the same force has to be applied to each of the connecting elements 11, 12 to ensure that the movable standing plate $P_1$ remains in its horizontal starting position even when loaded. In the device shown by way of example in FIG. 2, the center of gravity S of the user has to be located at the distance B/2 from the edge of the movable standing plate $P_1$, i.e. at the center of the movable standing plate $P_1$, in order to distribute the force $F_G$ uniformly to both connecting elements 11, 12. A force $F_{111}=F_G/2$ or $F_{121}=F_G/2$ then acts respectively on the connecting elements 11, 12. When loaded, the connecting element 11 has a height $H_{112}$ ($H_{112}=H_{111}-y_{111}$) and the connecting element 12 has a height $H_{122}$ ($H_{122}=H_{121}-y_{121}$) if the center of gravity S of a person is located at the center of the movable standing plate, i.e. $H_{112}=H_{122}$.

Figure 3:
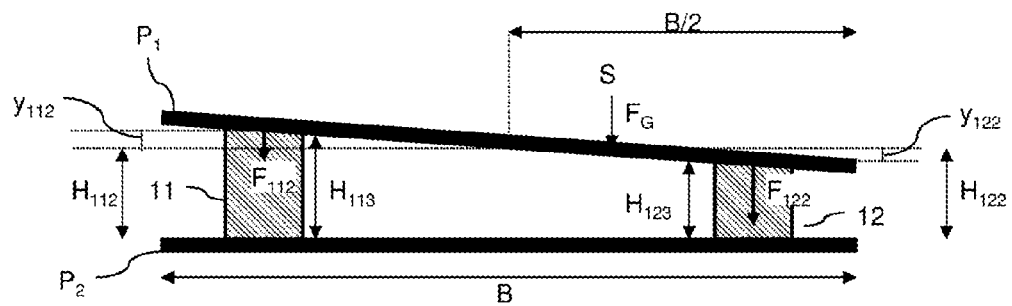
FIG. 3 shows by way of example the general principle of a device for training coordinative faculties with a movable standing plate.

As a result of a change of the position of the center of gravity S, the force $F_G$ is no longer distributed uniformly on the connecting elements 11, 12, and instead a greater force is applied to one of the connecting elements 11 or 12 than to the other one. As a result of a shift in the center of gravity, the movable standing plate $P_1$ can thus be inclined, by means of the connecting elements 11 and 12 being changed differently in terms of their height H as a result of the different forces acting on them. In FIG. 3, for example, the center of gravity S has shifted in the direction of the connecting element 12 from the starting position at B/2. As a result of the greater force now acting on the connecting element 12 (e.g. $F_{122}=\frac{2}{3} F_G$), the latter is reduced in height by $y_{122}$ compared to the loaded state in FIG. 2 ($H_{123}=H_{122}-y_{122}$). The connecting element 11, which now experiences less force than in the loaded starting state (e.g. $F_{112}=\frac{1}{3} F_G$), now has a height $H_{113}$ ($H_{113}=H_{112}+y_{112}$). The movable plate $P_1$ is therefore no longer horizontal and instead slopes downward in the direction of the connecting element 12.

Figure 4:
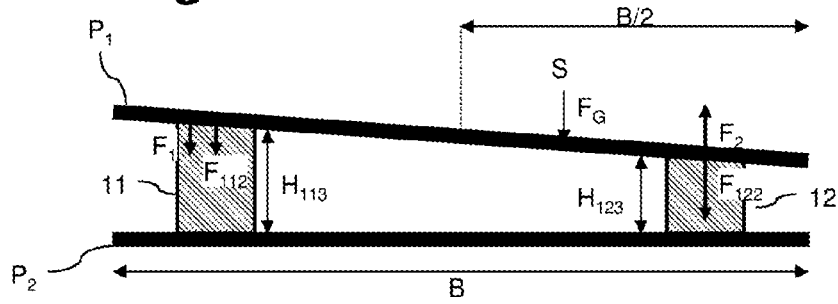
FIG. 4 shows by way of example the general principle of a device for training coordinative faculties with a movable standing plate.

However, the connecting elements 11, 12 can also be configured in such a way that they themselves can actively apply a force to the movable standing plate $P_1$. For example, the connecting elements 11, 12 can in this case be controlled individually, such that the movements are not generated by means of eccentrics from superposed sinus oscillations. For example, 1D, 2D or 3D trajectories can be specified or can be generated by a random generator. Individual impulses can also be generated. By means of the force generated by the connecting elements 11, 12, the movable standing plate $P_1$ can be forced away for example from the fixed base plate $P_2$ or drawn toward the fixed base plate $P_2$. In FIG. 4, for example, the connecting element 11 applies a force $F_1$ to the movable standing plate $P_1$, which force $F_1$ acts in the direction of the fixed base plate $P_2$. The force $F_1$ thus acts in the direction of the force $F_{112}$. By contrast, in the example shown, the connecting element 12 applies a force $F_2$ to the movable standing plate $P_1$, which force acts in the direction away from the fixed base plate $P_2$. The force $F_2$ thus acts counter to the force $F_{122}$. In this way, it is possible to counteract a shift in the center of gravity of the user. It is thus made difficult for the user to move his center of gravity S to a desired position. However, it is also possible, for example, that the force $F_1$ exerted by the connecting element 11 acts away from the fixed base plate $P_2$, i.e. counter to the force $F_{112}$, and the force $F_2$ exerted by the connecting element acts in the direction of the fixed base plate $P_2$, i.e. in the direction of the force $F_{122}$. In this way, for example, a shift of the center of gravity of the user can be supported. It is thus easier for the user to bring his center of gravity S to a defined position.

Figure 5:
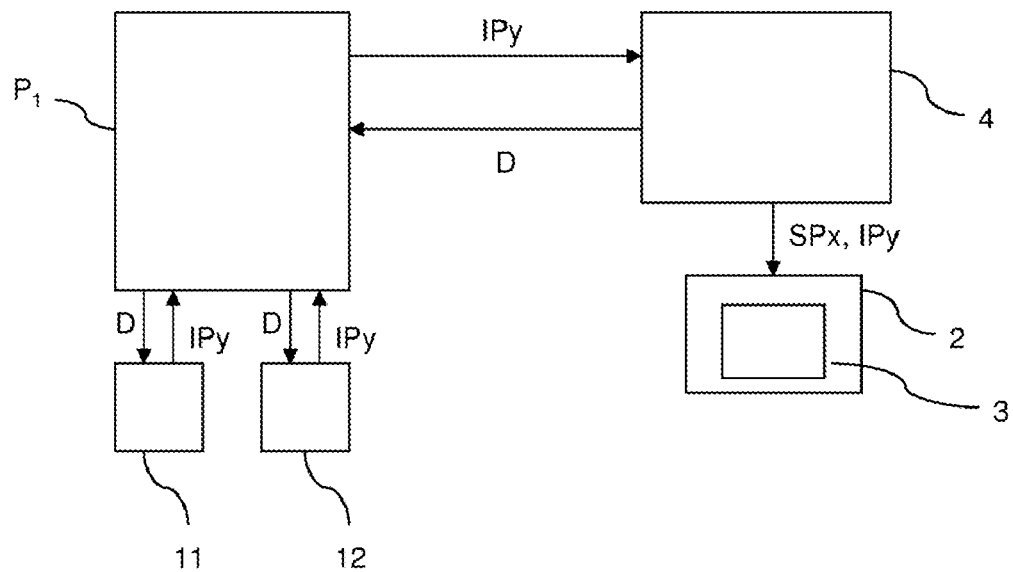
FIG. 5 shows, in a block diagram, an example of a control circuit for operating a device for training coordinative faculties with a movable standing plate.

On the basis of a block diagram, FIG. 5 shows an example of the basic principle of a control of a device according to the system described herein for training coordinative faculties with a movable standing plate $P_1$. The movable standing plate $P_1$ is connected to the connecting elements 11, 12 and to a control element 4. The control element 4 can, for example, specify a setpoint position SPx of the center of gravity S of a user present on the movable standing plate $P_1$ (e.g. as a function of time). The control element 4 can also be connected to a user interface 2 which, for example, has a display unit 3, for example a screen or the like, on which the specified setpoint position SPx can be shown graphically. The display unit 3 can, for example, be correspondingly connected to the user interface 2, although it can also be integrated in the user interface 2. The control element 4 can additionally send control signals D to the movable standing plate $P_1$, in order to control the connecting elements 11, 12 in such a way that they either disturb or support the movement of the user.

A user standing on the movable standing plate $P_1$ can then attempt to bring his center of gravity S to the specified setpoint position SPx. The sensors of the movable standing plate $P_1$ can be configured to measure continuously the actual position IPy of the center of gravity S of the user present on the movable plate $P_1$. Generally, "measuring" is also understood as an indirect measurement in which the actual measurement result (the center of gravity or the center of pressure) is calculated from other measured parameters. For example, the disturbance force ($F_G$) exerted on the connecting elements 11, 12 can be measured in order to calculate therefrom the actual position IPy of the center of gravity S. Alternatively, the center of gravity S can be estimated from the inclination of the movable standing plate $P_1$. However, any other methods suitable for measuring the center of gravity S are also possible here. The respectively measured actual position IPy of the center of gravity S at a measurement time $t_{My}$ can then be transmitted to the control element 4 for example. From the control element 4, information concerning the measured actual position IPy is in turn sent to the user interface 2. Then, for example, the measured actual positions IPy of the center of gravity S can be shown graphically by means of the display unit 3. In this way, the user can see where his center of gravity S is located in relation to the specified setpoint position SPx and in which direction he has to incline the movable standing plate $P_1$ by shifting his weight, so as to bring actual position IPy and setpoint position SPx into coincidence. A complete coincidence of setpoint position SPx and actual position IPy is not really possible in practice, especially if each setpoint position SPx is specified for only a short time period $t_{SPx}$, in order thereby to specify a more or less rapid setpoint movement that the user is intended to follow. For this reason, for example, different distance measurements can be used to assess a coincidence.

The device can have various modes or degrees of difficulty. In a first, easy mode, the connecting elements 11, 12, for example, can provide a mainly supporting action and guide the center of gravity S of the training user to the correct setpoint position SPx. The specified setpoint position SPx can, for example, be displayed for a relatively long time period $t_{SPx}$, such that the user has a long time available to him to bring the movable plate $P_1$, or the actual position IPy of his center of gravity S on the plate $P_1$, into coincidence with the corresponding setpoint position SPx (IPy=SPx, or Ipy~SPx). In an easy mode, the setpoint positions SPx could also be chosen, for example, in such a way that only a slight inclination of the movable plate $P_1$ by the user is necessary to bring actual position IPy and setpoint position SPx into coincidence. This is the case, for example, when the setpoint position SPx lies near the center point of the movable standing plate $P_1$. In this way, the movement of the movable plate $P_1$, in an easier mode for example, can as it were be damped and very safe.

In more difficult modes, the connecting elements 11, 12, for example, can increasingly counteract the movement of the training user as the degree of difficulty increases and push the center of gravity S thereof away from the setpoint position SPx. The disturbance can be generated randomly, for example. In a more difficult mode, for example, the individual setpoint positions SPx can also be displayed for an even shorter time period $t_{SPx}$, such that the user has only little time to bring his center of gravity S to the corresponding actual position IPy (IPy=SPx). If different successive setpoint positions SPx, for example, are each displayed for only a very short time period $t_{SPx}$, a more or less rapid setpoint movement of the center of gravity S can be specified that the user has to follow. Such a setpoint movement could, for example, become quicker and quicker as the difficulty increases. In a difficult mode, for example, a very pronounced inclination of the movable plate $P_1$ could also be necessary in order to bring the actual position IPy into coincidence with the specified setpoint position SPx. This can be achieved by the setpoint position SPx being specified farther toward the edges of the movable plate $P_1$.

The following modes among others are therefore conceivable for an arrangement with a movable standing plate $P_1$:

Mode M1: Control of the stiffness of the plate→active balance by the user.

Mode M2: Active balance by the user→random disturbance by the plate.

Mode M3: Active balance by the user→disturbance by the plate depending on the position of the center of gravity (center of pressure (COP)).

Mode M4: Movement program→active balance by the user, plate is set to "soft", measuring the time needed for stabilizing.

Mode M5: Safety mode→only certain movements of the plate are possible (e.g. right/left), if the plate tilts in other directions (e.g. forward), safety by active counter-control of the plate with the aid of the connecting elements 11, 12.

Mode M6: Active balance by the user→active movement program of the plate, continuous measurement of the center of gravity S.

The control element 4 can incorporate the results of the measurements of the actual position IPy, for example, in the generation of further setpoint positions SPx (or a complete sequence of setpoint positions, i.e. a setpoint trajectory of the center of gravity of the user). Moreover, it is possible, for example, to control the connecting elements 11, 12 by incorporating the results of the measurements of the actual positions IPy. Control can be effected, for example, by means of control signals D which are made available by the control element 4.

By comparing the specified setpoint positions SPx with the respectively measured actual positions IPy, it is possible to determine, for example, whether the current mode corresponds to the current training status of the user. For this purpose, it is possible, for example, to determine whether the user is at all able to bring the actual position IPy into coincidence with the respective setpoint position SPx, or how near the user can bring the actual position IPy to the respectively specified setpoint position SPx. However, it is also possible, for example, to determine the time needed by the training person to bring actual position IPy and setpoint position SPx into coincidence or to a defined distance from each other. For this purpose, for example, the actual position IPy can be measured several times with a time $t_{SPx}$ during which a setpoint position SPx is specified. As soon as a coincidence is established between for example a first setpoint position SP1 and an actual position IP1 (SP1=IP1), a next setpoint position SP2 can then be specified, for example.

However, it is also possible to determine only whether, within the specified time $t_{SPx}$ during which a setpoint position SPx is specified, the actual position IPy was brought into coincidence with this setpoint position SPx, without measuring the time needed for this. Alternatively or in addition, it is also possible, for example, to determine how long the actual position IPy is held in complete or almost complete coincidence with the setpoint position SPx, or how much an actual trajectory of the center of gravity of the user deviates from a specified setpoint trajectory at most or on average. Moreover, the speed with which the actual position IPy is changed, the center of pressure error integral (=surface), the frequency and/or the phase between a periodic actual movement and an associated setpoint movement of the center of gravity could be measured.

However, by continuous measurement of the actual position IPy of the center of gravity S, any tendency of the training person to fall can also be detected. For example, it is possible to detect whether a person is often in danger of falling in a certain direction (e.g. forward, backward or sideways). By detecting an individual dangerous tendency of this kind, it can be taken into consideration accordingly in the further training course. It is thus possible to very specifically train the individual weak points of each person training.

To detect progress in training, a total points count can be made, for example. If, after a measurement of the actual position IPy, a (substantial) coincidence is found between setpoint position SPx and actual position IPy, it is possible, for example, for a certain number of points to be added to this total points count. For example, if there is coincidence between setpoint position SPx and actual position IPy, a certain maximum number of points can be added. However, it is also possible, for example, to consider the distance of the measured actual positions IPy from the respectively specified setpoint position SPx. If actual position IPy and setpoint position SPx do not match but the actual position IPy has at least been brought close to the setpoint position SPx, a certain number of points can also be added to the total points count, for example for certain distances of the actual position IPy from the setpoint position SPx or for the periods of the match. That is to say, the shorter the distance between the setpoint position and actual position of the center of gravity, and the longer the user is able to maintain this short distance, the more points are credited to the points count. With longer measured distances of the actual position IPy from the setpoint position SPx, the added number of points can always be less, for example. Likewise, it is also possible, for example, to add more points the more quickly the actual position IPy was brought into coincidence with the setpoint position SPx. Alternatively or in addition, however, points can also be added according to any other desired criteria.

Figure 6:
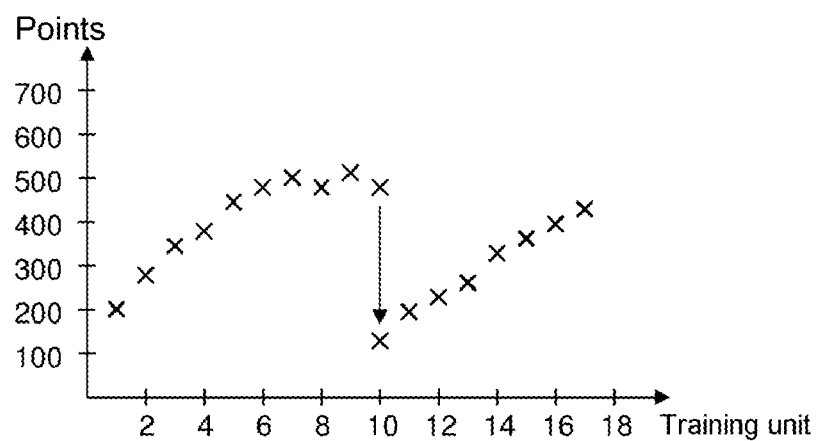
FIG. 6 shows, in a diagram, an example of a training course covering several training units.

If a first mode M1 is initially set, it is possible in this mode M1, for example, for the user to collect points by bringing the actual position IPy exactly or almost exactly into coincidence with the specified setpoint position SPx. For example, the points collected by the user (corresponding to the success of the user as measurable by predefinable criteria) can then be added up over the course of this training unit. An example of this is shown in the diagram in FIG. 6. The number of completed training units is plotted on the x axis, while the number of points achieved in total is plotted on the y axis.

The user begins, for example, in training unit 1. During this training unit, various setpoint positions SPx (e.g. along a setpoint trajectory) are specified. For example, for each match between actual position IPy and setpoint position SPx, a certain number of points can be achieved, which is added to the total points score. In the course of the first training unit, in the example shown, the user reaches a total points score of 200 points. In the following training units, the user improves in each case by a certain number of points and, for example from the seventh training unit, a stabilization phase begins in the example shown. From the seventh to the tenth training unit, the user in each case reaches a points score of about 500 points, i.e. remains relatively constant. A stabilization phase of this kind, subsequent to an improvement phase, can often be observed during a course of training. The attaining and maintaining of such a stabilization phase can thus be seen, for example, as an indication that the user has now mastered the current mode M1 so well that he can now train further in a second, more difficult mode M2.

On account of the increased difficulty in the second mode M2, the user once again initially achieves a low number of points per training unit, but he improves again from training unit to training unit. A changeover to a next mode can again be made, for example, when it has been detected that the user has already mastered the second mode M2, i.e. a stabilization phase has been attained once again. However, the detection of a stabilization phase is only one possible indication that the current mode is possibly no longer sufficiently demanding. For example, further indications could be that a user exceeds a certain number of points at the very start of a mode or that the actual position IPy is always measured in direct proximity (so-called target circle) to the setpoint position SPx.

However, it is likewise possible to detect, on the basis of various criteria, whether the selected mode is possibly too demanding. For example, if a certain minimum points score is not achieved over the course of a specified number of training units or no improvement phase is observed over the course of several training units, this can be used, for example, as an indication that the selected mode is too demanding for the user. Likewise, for example, measured falling tendencies could indicate that the current mode does not correspond to the current training status of the user. In such a case, it is possible to switch manually or automatically to an easier mode. In the automatic mode, active detection by the user and manual switching to another, suitable mode are not necessary.

With a device according to the system described herein, it is thus possible for the training level to be adjusted manually or also automatically, on the basis of various criteria, to the current training status of the user. In this way, a user never finds the training boring or too difficult and therefore demotivating.

Figure 7:
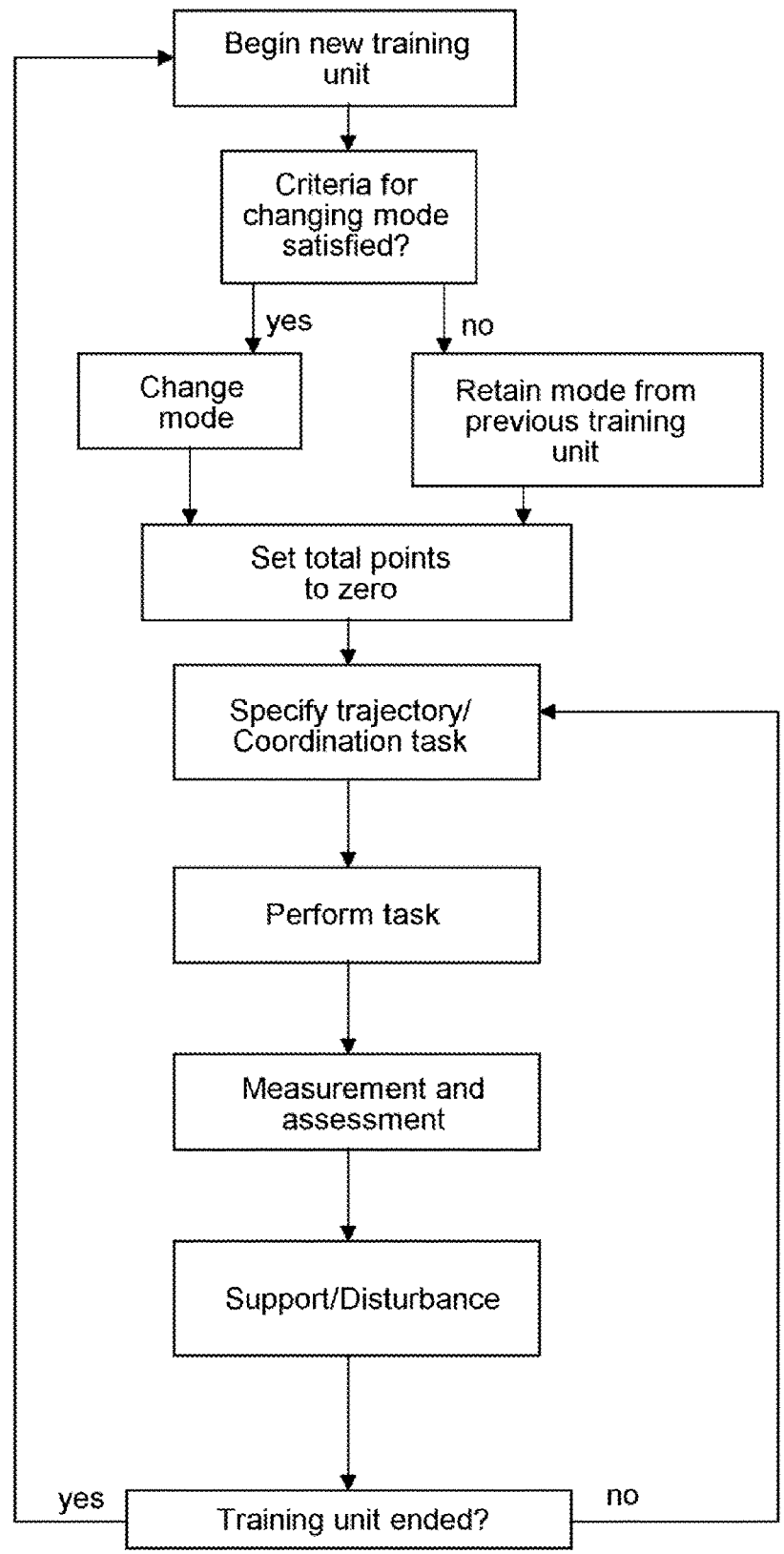
FIG. 7 shows by way of example a possible sequence of the information processing during the operation of a device for training coordinative faculties with a movable standing plate.

FIG. 7 shows an example of a possible sequence of the information processing during the operation of the device. Firstly, at the start of a new training unit, it is ascertained, for example, in which mode the user should train. If no training unit was completed beforehand, it is possible to start in an easy mode. If training units were already completed, then it is possible, for example on the basis of the abovementioned criteria, to determine whether the last mode should be retained, or whether an easier or more difficult mode should be adopted. Moreover, if present, a total points status can be reset to zero for the new training unit.

In accordance with the mode set, it is then possible, for example by means of the control element 4, to specify a setpoint position SPx, a setpoint movement or a coordination task. The user then has the possibility, for example during a time period $t_{SPx}$, to bring the actual position IPy into coincidence with the setpoint position SPx or to follow the setpoint movement as well as possible, or perform the set task. During the time period $t_{SPx}$, the actual position IPy of the center of gravity S is measured continuously. Each measured actual position IPy can then be compared with the setpoint position SPx specified at the measurement time $t_{My}$. Thereafter, an assessment can be made on the basis of this comparison. If the setpoint position SPx and the measured actual positions IPy match (almost, within certain tolerance ranges), the total points status can be increased, for example. If setpoint positions SPx and actual positions IPy do not match, the total points status can remain unchanged or be reduced, for example.

Depending on the degree of difficulty of the current mode, a (net) force F can be exerted on the movable standing plate $P_1$ by the connecting elements 11, 12. The force F applied to the movable standing plate $P_1$ can then act in the direction of (support) or against (disturbance) the force $F_G$ exerted by the user, wherein the force F, however, can also be zero for example.

If the end of the training unit is not yet reached, a new setpoint position SPx, setpoint movement or coordination task can be specified, and the above-described sequence is repeated. If the end of the training unit is reached, a next training unit can be started directly thereafter or at a later time, and the above-described sequence is accordingly repeated, after first testing whether the mode should be changed. An integrated closed control circuit is obtained in this way.

To allow the movable plate $P_1$ to be actively influenced by the system, the connecting elements 11, 12 can be configured accordingly. For example, active, controllable mechanical actuating elements, e.g. bellows cylinders or air muscles, can be used as connecting elements 11, 12. However, other connecting elements are also conceivable here which can be changed in terms of their height H by the weight of the user and in addition can actively apply a force F to the movable standing plate $P_1$. The connecting elements can then be correspondingly controlled for example via the control element 4 by means of control signals D.

Figure 8:
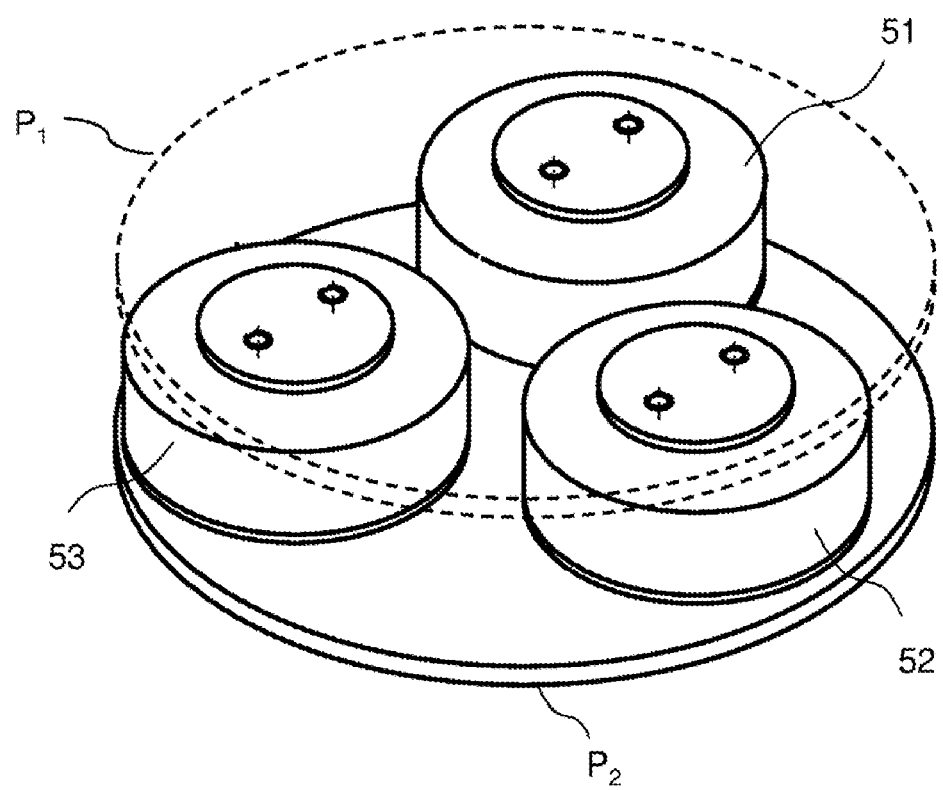
FIG. 8 shows a schematic representation of a further example of a device for training coordinative faculties with a movable standing plate.

FIG. 8 shows a simplified example of a device of this kind. In the example shown, the movable standing plate $P_1$ has a round shape. The movable standing plate $P_1$ is connected to a fixed base plate $P_2$ by means of three connecting elements 51, 52, 53. In the example shown, the connecting elements 51, 52, 53 are configured as bellows cylinders. However, as has already been explained above, it is also possible to provide other kinds of connecting elements here that are modifiable in terms of their height and that can actively apply a force to the movable standing plate $P_1$. In the arrangement shown, the connecting elements 51, 52, 53 are arranged in such a way that they form an equilateral triangle. With such an arrangement, for example, an inclination of the movable standing plate $P_1$ is possible about several axes. However, the illustrated arrangement of the connecting elements 51, 52, 53 is given only as an example, and other arrangements are also conceivable.

The described examples are intended merely to illustrate the basic principle of the device according to the system described herein. The device can be used not just to train humans but also, for example, to train animals. Moreover, various other embodiments are possible. Instead of a single movable standing plate, it is also possible for several standing plates to be provided. If the device is to be used, for example, to train horses, a standing plate can be provided for each hoof, i.e. four standing plates. The center of gravity can then be measured, for example, by determining the tilt angles of the plates or by means of other suitable methods, and each individual standing plate can be controlled in the manner explained above.

When using a plurality of standing plates, modes M1 to M5, for example, can be provided, as in the manner described for the single movable standing plate. Alternatively or in addition, however, the following modes can also be implemented:

Mode M7: Measurement of center of gravity left/right interpolation.

Mode M8: Measurement of center of gravity from the tilt angles (forward/backward) of the plates.

Other embodiments of the invention will be apparent to those skilled in the art from a consideration of the specification or practice of the invention disclosed herein. It is intended that the specification and examples be considered as exemplary only, with the true scope and spirit of the invention being indicated by the following claims.

The invention claimed is:

1. A device, comprising:
a standing plate;
a base plate;
two or more actuators coupled to the standing plate and the base plate to modify an inclination of the standing plate in relation to the base plate; and
a control element that operates in a plurality of modes associated with respective control characteristics and drives the actuators to provide a set-point position of a center of gravity of a user present on the standing plate in accordance with a control characteristic associated with a selected mode of the plurality of modes,
wherein the modes are difficulty modes, each mode associated with a specific degree of difficulty represented by the control characteristic associated with the respective difficulty mode, and
wherein the control element drives the actuators such that they increasingly counteract the movement of the user as the degree of difficulty increases and push the center of gravity thereof away from the set-point position.

2. The device of claim 1, wherein, in a first mode of the plurality of modes, the control element drives the actuators to cause the actuators to at least partly counteract a movement of the user by pushing an actual position of the center of gravity of the user away from the set-point position of the center of gravity in accordance with a control characteristic of the first mode.

3. The device of claim 1, wherein, in a first mode of the plurality of modes, the control element drives the actuators to cause the actuators to provide a substantially supporting action and guide an actual position of the center of gravity of the user to the set-point position in accordance with a control characteristic of the first mode.

4. The device as claimed in claim 1, wherein the control element specifies a sequence of different values for the set-point position to form a set-point movement for the user to follow.

5. The device as claimed in claim 1, wherein the control element specifies a sequence of set-point positions to form a set-point movement that the user is to follow, the set-point movement becoming increasingly quicker as the level of difficulty increases.

6. The device as claimed in claim 1, wherein the control element is configured to drive the actuators to cause an inclination of the at least one movable plate to be increasingly pronounced as a level of difficulty increases.

7. The device of claim 1, wherein the control element drives the actuators to cause the standing plate to be randomly disturbed when operating in a first mode of the plurality of modes.

8. The device of claim 1, wherein the control element continuously measures actual positions of the center of gravity of the user and uses the measured actual positions of the center of gravity to automatically generate further set-point positions.

9. The device of claim 1, wherein the control element continuously measures actual positions of the center of gravity and controls the actuators using the actual positions of the center of gravity.

10. The device as claimed in claim 9, wherein the control element automatically compares each of the actual positions of the center of gravity of the user with a corresponding one of the set-point positions and generates control signals to control the actuators according to a result of the comparison.

11. The device as claimed in claim 1, wherein the control element continuously measures actual positions of the center of gravity and automatically compares each of the actual positions with a corresponding one of the set-point positions, and wherein a changeover to a mode associated with a higher degree of difficulty is made depending on a result of the comparison.

12. The device of claim 1, wherein the control element determines a time needed by the user to bring an actual position of the center of gravity to a current setpoint position or to determine whether a position of the center of gravity and the current setpoint position are brought into coincidence within a specific time.

13. The device of claim 1, wherein the control element continuously measures actual positions of the center of gravity, wherein a total points count is made that represent progress in training, wherein for each training unit, if, after measurement of the actual positions of the center of gravity, a substantial coincidence is found between the set-point position and the actual position of the center of gravity of the user, a certain number of points is added to the total points count, and wherein a deviation between the actual position and the set-point position for a training unit results in less points being added to the total points count.

14. The device of claim 13, wherein a changeover to a more difficult mode is made when a stabilization phase has been attained based on a relatively stable total points score over a certain number of training units.

15. The device as claimed in claim 1, wherein the control element is configured to change to another mode of the plurality of modes in response to an input by the user via a user interface.

16. The device of claim 1, further comprising:
a display unit configured to give a graphic representation of a particular one of the set-point positions and a corresponding one of the actual positions of the center of gravity of the user.

17. The device of claim 1, wherein the actuators are actively controllable in height using mechanical actuating elements and wherein the mechanical actuating elements include at least one of: linear motors, electric motors, hydraulic cylinders, bellows cylinders or air muscles.

18. A method of training coordinative faculties, comprising:
selecting a mode of a plurality of modes, each mode of the plurality of modes being associated with a respective control characteristic;
specifying a set-point position of a center of gravity of a user present on a standing plate; and
modifying an inclination of the standing plate with respect to a base plate by controlling two or more actuators coupled between the base plate and the standing plate in accordance with the control characteristic associated with a selected mode,
wherein the modes are difficulty modes, each mode associated with a specific degree of difficulty represented by the control characteristic associated with the respective difficulty mode, and
wherein the control element drives the actuators such that they increasingly counteract the movement of the user as the degree of difficulty increases and push the center of gravity thereof away from the set-point position.

19. The method of claim 18, further comprising:
continuously measuring an actual position of the center of gravity of the user to provide a plurality of measured actual positions; and
using the measured actual positions to automatically generate additional set-point positions.

* * * * *